US010322089B2

(12) United States Patent
Lobovkina et al.

(10) Patent No.: US 10,322,089 B2
(45) Date of Patent: Jun. 18, 2019

(54) NANOPARTICLES, NANOPARTICLE DELIVERY METHODS, AND SYSTEMS OF DELIVERY

(71) Applicant: The Board of Trustees of the Leland Stanford Junior University, Palo Alto, CA (US)

(72) Inventors: Tatsiana Lobovkina, Menlo Park, CA (US); Gunilla B. Jacobson, Taby (SE); Richard N. Zare, Stanford, CA (US); Evgenios Neofytou, San Carlos, CA (US); Ramin E. Beygui, Hillsborough, CA (US); Marie Russo, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 858 days.

(21) Appl. No.: 13/799,883

(22) Filed: Mar. 13, 2013

(65) Prior Publication Data
US 2013/0243848 A1  Sep. 19, 2013

Related U.S. Application Data

(60) Provisional application No. 61/610,524, filed on Mar. 14, 2012.

(51) Int. Cl.
*A61K 9/51* (2006.01)
*A61K 47/54* (2017.01)

(52) U.S. Cl.
CPC .............. *A61K 9/51* (2013.01); *A61K 9/5123* (2013.01); *A61K 9/5192* (2013.01); *A61K 47/543* (2017.08)

(58) Field of Classification Search
None
See application file for complete search history.

(56) References Cited

U.S. PATENT DOCUMENTS

2006/0134189 A1*  6/2006  MacLachlan et al. ........ 424/450
2011/0256175 A1*  10/2011  Hope et al. ................ 424/204.1

FOREIGN PATENT DOCUMENTS

WO    WO-96-23409    *   1/1996

OTHER PUBLICATIONS

Lobovkina T, In vivo sustained release of siRNA from solid lipid nanoparticles, ACSNano, 2011, 5(12), 9977-9983.*
Dayton S, Composition of lipids in human serum and adipose tissue during prolonged feeding of a diet high in unsaturated fat, Journal of Lipid Research, 7, 1966, 103.*

* cited by examiner

*Primary Examiner* — Celeste A Roney
(74) *Attorney, Agent, or Firm* — Thomas|Horstmeyer, LLP

(57) ABSTRACT

In accordance with the purpose(s) of the present disclosure, as embodied and broadly described herein, embodiments of the present disclosure, in one aspect, relate to nanoparticles, compositions including nanoparticles, methods of making nanoparticles, and the like. In particular, embodiments of the present disclosure include nanoparticles and compositions for the sustained release (e.g., release at a predetermined rate to maintain a certain concentration for a certain period of time) of an agent, such as a small interfering RNA (siRNA) from the nanoparticle.

6 Claims, 3 Drawing Sheets

NANOPARTICLES, NANOPARTICLE DELIVERY METHODS, AND SYSTEMS OF DELIVERY

CLAIM OF PRIORITY TO RELATED APPLICATION

This application claims priority to U.S. provisional application entitled "NANOPARTICLES, NANOPARTICLE DELIVERY METHODS, AND SYSTEMS OF DELIVERY" having Ser. No. 61/610,524, filed on Mar. 14, 2012, which is entirely incorporated herein by reference.

STATEMENT REGARDING FEDERALLY SPONSORED RESEARCH OR DEVELOPMENT

This invention was made with Government support under contract CA125467 awarded by the National Institutes of Health. The Government has certain rights in this invention.

BACKGROUND

Although small interfering RNAs (siRNAs) hold promise as nucleic acid-based therapeutics, effective and well-controlled in vivo delivery remains challenging for two main reasons. First, crossing biological barriers such as the stratum corneum (for skin delivery), the cell membrane, and the endosomal compartment is difficult. Second, long-term therapeutic effects will require repeated dosing. We already know that unmodified siRNA molecules are not taken up efficiently by most cells owing to their size (~13,000 Mw) and anionic nature, and therefore may not result in effective gene silencing in vivo. Nanoparticles have the potential for meeting both challenges. Utilization of nanoparticles engineered for slow, sustained and controlled release of functional siRNA may decrease the frequency of treatment and lead to more effective therapies. To overcome the previously mentioned delivery challenges, lipid-based delivery systems, such as cationic liposomes and stable nucleic acid-lipid particle (SNALP), have been employed to mask the negative charges on the siRNA phosphodiester backbone and facilitate uptake. Building on this theme, other delivery vehicles based on the variety of cationic and biodegradable polymers have been developed, but many proposed approaches have demonstrated limited delivery of siRNA. Thus, other approaches are needed.

SUMMARY

In accordance with the purpose(s) of the present disclosure, as embodied and broadly described herein, embodiments of the present disclosure, in one aspect, relate to nanoparticles, compositions including nanoparticles, methods of making nanoparticles, and the like. In particular, embodiments of the present disclosure include nanoparticles and compositions for the sustained release (e.g., release at a predetermined rate to maintain a certain concentration for a certain period of time) of an agent, such as a small interfering RNA (siRNA) from the nanoparticle.

In an embodiment, the composition can include: a nanoparticle including a siRNA-cationic lipid conjugate, wherein the siRNA-cationic lipid conjugate is disposed within the nanoparticle.

In an embodiment, the composition can include: a nanoparticle including a siRNA-cationic lipid conjugate, wherein the nanoparticle has a lipid monolayer enclosing the nanoparticle core, wherein the siRNA-cationic lipid conjugate is disposed within the nanoparticle core. In an embodiment, the nanoparticle core includes a solid lipid (i.e., lipid that remains solid at room temperature and body temperature) or a liquid lipid (i.e., oil, which remains liquid at room temperature and body temperature, for example, vegetable oil or a lipid extracted from human adipose tissue).

In an embodiment, the method of making a solid lipid nanoparticle can include: providing a first organic phase solution that includes the siRNA-cationic lipid conjugate and a second organic phase solution that includes the solid lipid, providing a water-containing phase solution that includes the lipid layer lipid; mixing the first organic phase and the second organic phase with the aqueous phase and evaporate a portion of the mixture; and forming the solid lipid nanoparticle, wherein the solid lipid nanoparticle is a nanoparticle including a siRNA-cationic lipid conjugate, wherein the nanoparticle has a lipid monolayer enclosing the nanoparticle core, wherein the siRNA-cationic lipid conjugate is disposed within the nanoparticle core, and wherein the nanoparticle core includes a solid lipid.

In an embodiment, the method of making a solid lipid nanoparticle can include: providing an organic phase solution that includes the solid lipid and the siRNA-cationic lipid conjugate, providing an a water-containing phase solution that includes the lipid layer lipid and the nonionic surfactant; mixing the organic phase and the aqueous phase and evaporate a portion of the mixture; and forming the solid lipid nanoparticle, wherein the solid lipid nanoparticle is a nanoparticle including a siRNA-cationic lipid conjugate, wherein the nanoparticle has a lipid monolayer enclosing the nanoparticle core, wherein the siRNA-cationic lipid conjugate is disposed within the nanoparticle core, and wherein the nanoparticle core includes a solid lipid.

In an embodiment, the method of making a liquid lipid nanoparticle can include: providing an organic phase solution that includes the liquid lipid (i.e., oil), the siRNA-cationic lipid conjugate, and lipid layer lipid, providing an aqueous phase solution that include the nonionic surfactant; mixing the organic phase and the aqueous phase and evaporate a portion of the mixture; and forming the liquid lipid nanoparticle, wherein the liquid lipid nanoparticle is a nanoparticle including a siRNA-cationic lipid conjugate, wherein the nanoparticle has a lipid monolayer enclosing the nanoparticle core, wherein the siRNA-cationic lipid conjugate is disposed within the nanoparticle core, and wherein the nanoparticle core includes a liquid lipid.

Other systems, methods, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 4(a-c) illustrate images from frozen skin sections that were prepared from footpads treated by intradermal injection of siGLO Red SLNPs (the dose of siGLO Red is 8 g) for 3, 6, or 13 d. Red, siGLO Red; blue, Syto-62 stained nuclei and cytoplasma. Stratum corneum (sc), epidermis FIG. 4(e), and dermis FIG. 4(d).

DETAILED DESCRIPTION

Figure 1:
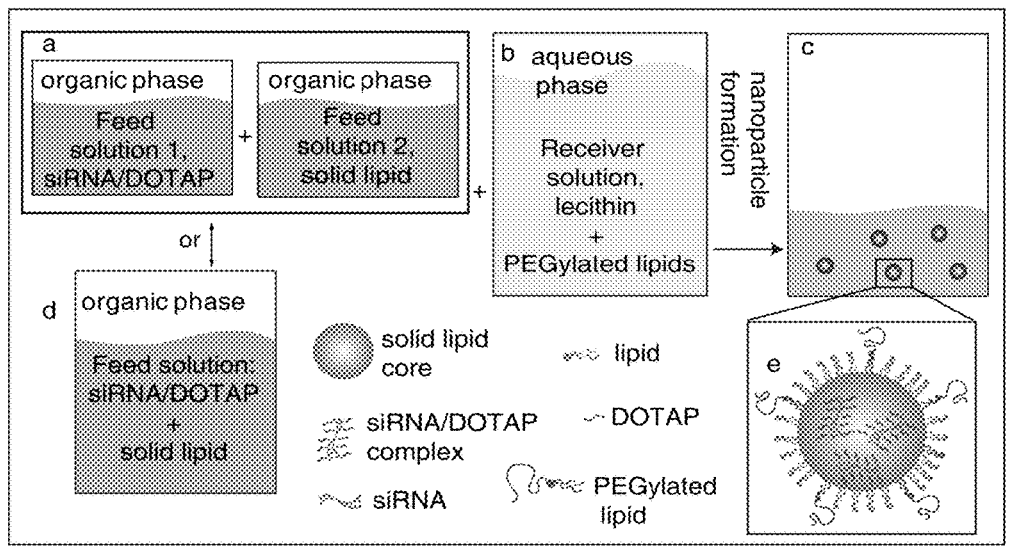
FIG. 1 illustrates a schematic drawing showing preparation of SLNPs with encapsulated siRNA molecules. Feed solutions 1 and 2 pictured in FIG. 1(a) are sequentially added to the receiver solution pictured in FIG. 1(b). SLNPs form following evaporation of organic solvents, as shown in FIG. 1(c). Alternatively, siRNA/DOTAP complex and tristearin are solubilised in CHF, as shown in FIG. 1(d), and then added to the aqueous receiver solution. A schematic drawing of SLNP is presented in FIG. 1(e). The sizes and ratios of components are not to scale for illustrative purposes.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biochemistry, biology, molecular biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

The term "administration" refers to introducing a composition (e.g., a nanoparticles, a composition including nanoparticles, or the like) of the present disclosure into a desired location in the subject. In an embodiment, once the composition is administered (e.g., injection) to the desired location of the subject. In an embodiment, administer includes orally, nasal, rectal, dermal, urogenital, intravenous, intramuscular, subcutaneous, intradermal, intraarticular, intrathecal, epidural, intracerebral, intraosseous, intraperitoneal, and the like.

In accordance with the present disclosure, "an effective amount" of the composition of the present disclosure is defined as an amount sufficient to yield an acceptable outcome (treatment of the condition or disease). In an embodiment, an effective amount of the composition of the present disclosure may be administered in one or more doses. The effective amount of the compositions of the present disclosure can vary according to factors such as the type of drug, the time frame and amount of released doses, degree of susceptibility of the individual, the age, sex, and weight of the individual, idiosyncratic responses of the individual, the dosimetry, and the like.

As used herein, "treat", "treatment", "treating", and the like refer to acting upon a disease, condition, or disorder with a composition to affect the disease, condition, or disorder by improving or altering it. The improvement or alteration may include an improvement in symptoms or an alteration in the physiologic pathways associated with the disease, condition, or disorder. "Treatment," as used herein, covers one or more treatments of a disease in a host (e.g., a mammal, typically a human or non-human animal of veterinary interest) using an embodiment of the present disclosure, and includes: (a) reducing the risk of occurrence of the disease, condition, or disorder in a subject determined to be predisposed to the disease but not yet diagnosed as infected with the disease, condition, or disorder, (b) impeding the development of the disease, condition, or disorder, and/or (c) relieving the disease, condition, or disorder, e.g., causing regression of the disease, condition, or disorder and/or relieving one or more disease, condition, or disorder symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a disease, condition, or disorder or symptom thereof and/or may be therapeutic in terms of a partial or complete cure for a disease, condition, or disorder and/or adverse effect attributable to the disease, condition, or disorder, using an embodiment of the present disclosure.

The term "unit dosage form," as used herein, refers to physically discrete units suitable as unitary dosages for human and/or animal subjects, each unit containing a predetermined quantity of a composition calculated in an amount sufficient (e.g., weight of host, disease, severity of the disease, etc) to produce the desired effect. The specifications for unit dosage forms depend on the particular composition employed, the route and frequency of administration, and the effect to be achieved, and the pharmacodynamics associated with the composition in the host.

The term "therapeutically effective amount" as used herein refers to that amount of an embodiment of the composition being administered that will relieve to some extent one or more of the symptoms of the disease, condition, or disorder being treated, and/or that amount that will prevent, to some extent, one or more of the symptoms of the disease, condition, or disorder that the host being treated has or is at risk of developing. Embodiments of the present disclosure can be administered in an therapeutically effective amount.

As used herein, the term "subject" or "host" includes humans and mammals (e.g., mice, rats, pigs, cats, dogs, and horses,). Typical subjects to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to host or organisms noted above that are alive. The term "living subject" refers to the entire host or organism and not just a part excised (e.g., a liver or other organ) from the living subject.

DISCUSSION

In accordance with the purpose(s) of the present disclosure, as embodied and broadly described herein, embodiments of the present disclosure, in one aspect, relate to nanoparticles, compositions including nanoparticles, methods of making nanoparticles, and the like. In particular, embodiments of the present disclosure include nanoparticles and compositions for the sustained release (e.g., release at a predetermined rate to maintain a certain concentration for a certain period of time) of an agent, such as a small interfering RNA (siRNA) from the nanoparticle. In an embodiment, the agent can be released over the course of hours to days to a week or more, unlike other techniques where the siRNA clears the subject in several hours or a day or two. In an embodiment, the nanoparticles can be designed so that they can include agents so that they can be imaged, target specific diseases, conditions, or chemicals associated with the disease or condition, increase biocompatibility, and the like. Thus, embodiments of the present disclosure can be multifunctional. Additional details regarding the sustained release of the compound and methods of making the nanoparticles, will be described in more detail below and in the Examples.

In an exemplary embodiment, the composition includes a nanoparticle that includes a siRNA-cationic lipid conjugate disposed within the nanoparticle or inside of the nanoparticle. In an embodiment, the siRNA is released over a time frame of hours to days to weeks at a predetermined rate from the nanoparticle core and a lipid layer (e.g., lipid monolayer) enclosing the nanoparticle core. In an embodiment, the sustained release of the siRNA can be controlled by what is disposed in the nanoparticle core, the lipid layer, the siRNA-cationic lipid conjugate, agents disposed on the surface of the nanoparticle, and/or the environment outside of the nanoparticle. Although the siRNA-cationic lipid conjugate or the siRNA could be located on the surface of the nanoparticle, most of or all of the sustained release portion of the siRNA-cationic lipid can be disposed within the nanoparticle. In an embodiment, the nanoparticle can have a diameter of about 150 to 800 nm.

In an embodiment, the siRNA are drugs that can be used in gene-based therapy. In general, siRNA can include about 20-25 nucleotides in length and are double stranded RNA molecules. In an embodiment, the siRNA interfere with the expression of specific genes. In an embodiment, any siRNA can be used in an embodiment of the present disclosure. In an embodiment, each nanoparticle can be loaded with about 0.5 to 6 weight percent or about 4 weigh percent of siRNA.

In an embodiment, a purpose of the cationic lipid is to assist in the introduction of the siRNA into the hydrophobic core of nanoparticle and/or assist in the sustained release of the siRNA from the nanoparticle. Using a cationic lipid component in this way can be referred to as hydrophobic ion pairing (HIP). In an embodiment, the cationic lipid can be attached to the siRNA using electrostatic forces and then introduced into the nanoparticle using one or more techniques. In an embodiment, the cationic lipid is selected from the group consisting of: DOTAP (1,2-dioleoyl-3-trimethyl-ammonium-propane), DC-cholesterol (DC-Cholesterol.HCl 3β-[N-(N',N'-dimethylaminoethane)-carbamoyl]cholesterol hydrochloride), DODAP (1,2-dioleoyl-3-dimethylammonium-propane), DDAB (dimethyldioctadecylammonium), Ethyl PC (1,2-dilauroyl-sn-glycero-3-ethylphosphocholine), DOTMA (2-di-O-octadecenyl-3-trimethylammonium propane), and a combination thereof.

In an embodiment, the nanoparticle includes a lipid layer (e.g., lipid monolayer) enclosing the nanoparticle core where the siRNA-cationic lipid is entrapped. In an embodiment, the lipid layer can be about 2 to 10 nm or about 5 nm. In an embodiment, the lipid layer can be a lipid monolayer. In an embodiment, the lipid layer can include two or more lipid layers. In an embodiment, the lipid layer can be selected from: phospholipids such as lecithin, (L-α-phosphatidylcholine) or phosphatidylcholines with saturated and unsaturated fatty acids. In an embodiment, the lipid layer may also contain other phospholipids, such as phosphatidic acids, phosphatidylethanolamines, phosphatidylglycerols, phosphatidylserines, phosphatidylinositols, cardiolipins, or a combination thereof. In embodiment, the lipid layer can include lipid-PEG (lipid-polyethyleneglycol) conjugates with various molecular weight of PEG in the range of 350-3500 or larger.

In an embodiment, the nanoparticle can be a solid lipid nanoparticle. In an embodiment, the solid lipid nanoparticle includes a lipid layer enclosing the nanoparticle core (as described herein), where a solid lipid can be disposed in the nanoparticle core along with the siRNA-cationic lipid conjugate. In embodiment, the solid lipid can be a lipid that remains a solid at the body temperature of the subject, so that the solid lipid can be selected based on the subject. In an embodiment, the solid lipid can be selected from the following group: monoglycerides (e.g. glycerol monostearate), diglycerides (e.g., glycerol bahenate), triglycerides (e.g., tristearin, trimyristin, trilaurin), waxes (e.g., cetyl palmitate), fatty acids (e.g., stearic acid, palmitic acid), steroids (e.g., cholesterol), and a combination thereof.

In an exemplary embodiment, the solid lipid nanoparticles can be made by first making an organic phase solution that includes the solid lipid or precursors thereof and the siRNA-cationic lipid conjugate. Alternatively, two organic solutions can be prepared separately, one containing siRNA-cationic lipid complex, and another one containing solid lipids. A water-containing phase solution can be prepared that includes the lipid from outer layer lipid. The aqueous phase solution can be mixed with the organic phase or can be mixed with the first organic phase and second organic phase sequentially in any order, or mixed simultaneously. In an embodiment, the mixture can be mixed and heated, and a portion of the mixture can be evaporated. Subsequently, the solid lipid nanoparticles are formed. In an embodiment, the solid lipid nanoparticle can include one or more of the agents described herein. The method for making the solid lipid nanoparticle can be modified to incorporate one or more agents. Additional details regarding the method of making the solid lipid nanoparticles is described in the Example.

In an embodiment, the nanoparticle can be a liquid lipid nanoparticle, i.e. oil-in-water nanoemulsions. In an embodiment, the liquid lipid nanoparticle includes a lipid layer enclosing the nanoparticle core (as described herein), where a liquid lipid can be disposed in the nanoparticle core along with the siRNA-cationic lipid conjugate. In an embodiment, the liquid lipid can be a lipid that remains a liquid at the body temperature of the subject, so the liquid lipid can be selected based on the subject. In an embodiment, the liquid lipid can be selected from the following: soybean oil, peanut oil, sunflower oil or other vegetable oils, as well as lipids extracted from adipose tissue, and a combination thereof. In an embodiment, a surfactant can be used to stabilize the formation of the liquid lipid nanoparticle and the surfactant (e.g., lecithin and other phospholipids, lipid-PEG) can be included in the liquid lipid. Advantages of using the lipids extracted from adipose tissue are described in the Example.

In an exemplary embodiment, the liquid lipid nanoparticles can be made by making an organic phase solution that includes the liquid lipid (e.g., oil) and the siRNA-cationic lipid conjugate, and/or the lipid layer lipids. In an embodiment, a water-containing phase solution can be made that includes nonionic surfactant and/or the lipid layer lipids. The organic phase solution and the aqueous phase solution can be mixed and then optionally sonicated to form a nanoemulsion or a crude emulsion. Subsequently the crude emulsion is optionally sonicated or filtering the mixture through a porous membrane filter to form a nanoemulsion that includes the liquid lipid nanoparticles. In an embodiment, the liquid lipid nanoparticle can include one or more of the agents described herein. The method for making the liquid lipid nanoparticle can be modified to incorporate the one or more agents. Additional details regarding the method of making the liquid lipid nanoparticles is described in the Examples.

In an exemplary embodiment, one or more agents can be disposed within the nanoparticle core along with the siRNA-cationic conjugate and optionally with the solid lipid or liquid lipid. In particular, the agent can include a drug, an imaging agent, a surfactant (e.g., Pluroinic F68, Tween 80, polyvinyl alcohol, and the like), an imaging agent, a biocompatibility agent, other types of lipids, and a combination thereof. In an embodiment, the amount of the agent can depend upon the type of agent, the amount of the composition, the subject, the purpose of the agent, the siRNA-cationic lipid conjugate, and the like.

In an exemplary embodiment, one or more agents can be disposed on the outside surface (e.g., directly attached or attached via a linking group) of the nanoparticle core. In particular, the agent can include a drug, an imaging agent, a biocompatibility agent, other types of lipids, surfactant (e.g., Pluroinic F68, Tween 80, polyvinyl alcohol, and the like), and a combination thereof. In an embodiment, the amount of the agent can depend upon the type of agent, the amount of the composition, the subject, the purpose of the agent, the siRNA-cationic lipid conjugate, and the like.

In an exemplary embodiment, the targeting agent can have an affinity for a cell, a tissue, a protein, DNA, RNA, an antibody, an antigen, and the like, that may be associated with a condition, disease, or related biological event, of interest. In particular, the targeting agent can function to target specific DNA, RNA, and/or proteins of interest. The targeting agent can include, for example, polypeptides (e.g., proteins such as, but not limited to, antibodies (monoclonal or polyclonal)), antigens, nucleic acids (both monomeric and oligomeric), polysaccharides, sugars, fatty acids, steroids, purines, pyrimidines, ligands, aptamers, small molecules, ligands, or combinations thereof, and the like, that have an affinity for a condition, disease, or related biological event or other chemical, biochemical, and/or biological events of the condition, disease, or biological event.

In an exemplary embodiment, the biocompatibility agent can be synthetic polymers, such as, n-monoethylene glycol (n-MEG), a poly(ethylene glycol) (PEG), poly(vinyl alcohol) (PVA), poly(acrylic acid) (PAA), poly(propylene furmarate-co-ethyleenee glycol) (P(PF-co-EG)), polyacrylamide, polypeptides, poly-N-substituted glycine oligomers (polypeptoids), combinations thereof, and the like, while naturally derived biocompatibility agent polymers normally include hyaluronic acid (HA), alginate, chitosan, agarose, collagen, fibrin, gelatin, dextran, and any combination thereof, combinations thereof, as well as derivatives of each of these, and the like.

In an exemplary embodiment, the drug can include, for example, a small molecule drug, a chemotherapy drug, a radiotherapy drug, a photodynamic therapy drug, a biological drug, imaging agent, other types of oligonucleotides than siRNA i.e. small hairpin RNA (shRNA), or microRNA (miRNA), combinations thereof, and the like.

In an exemplary embodiment, the imaging agent can include, for example, an MRI imaging agent, PET imaging agent, SPECT imaging agent, luminescent imaging agent, bioluminescent imaging agent, fluorescent imaging agent, radiological imaging agent, ultrasound imaging agent, combinations thereof, and the like.

EXAMPLES

Now having described the embodiments of the present disclosure, in general, the examples describe some additional embodiments of the present disclosure. While embodiments of the present disclosure are described in connection with examples and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

Brief Introduction

Small interfering RNA (siRNA) is a highly potent drug in gene-based therapy with a challenge of being delivered in a sustained manner. Nanoparticle drug delivery systems allow for incorporating and controlled release of therapeutic payloads. We demonstrate that solid lipid nanoparticles can incorporate and provide sustained release of siRNA. Tristearin solid lipid nanoparticles, made by nanoprecipitation, were loaded with siRNA (4.4-5.5 weight percent loading ratio) using a hydrophobic ion pairing approach that employs the cationic lipid DOTAP. Intradermal injection of these nanocarriers in mouse footpads resulted in prolonged siRNA release over a period of 10-13 days. In vitro cell studies showed that the released siRNA retained its activity. Nanoparticles developed in this study offer an alternative approach to polymeric nanoparticles for encapsulation and sustained delivery of siRNA with the advantage of being prepared from physiologically well-tolerated materials.

Introduction

Although small interfering RNAs (siRNAs) hold promise as nucleic acid-based therapeutics, effective and well-controlled in vivo delivery remains challenging for two main reasons. First, crossing biological barriers such as the stratum corneum (for skin delivery), the cell membrane, and the endosomal compartment is difficult.[1-5] Second, long-term therapeutic effects will require repeated dosing. We already know that unmodified siRNA molecules are not taken up efficiently by most cells owing to their size (~13,000 Mw) and anionic nature, and therefore may not result in effective gene silencing in vivo.[6] Nanoparticles have the potential for meeting both challenges. Utilization of nanoparticles engineered for slow, sustained and controlled release of functional siRNA may decrease the frequency of treatment and lead to more effective therapies. To overcome the previously mentioned delivery challenges, lipid-based delivery systems, such as cationic liposomes and stable nucleic acid-lipid particle (SNALP), have been employed to mask the negative charges on the siRNA phosphodiester backbone and facilitate uptake.[7-9] Building on this theme, other delivery vehicles based on the variety of cationic and biodegradable polymers have been developed.[10-15] Many proposed approaches have demonstrated limited delivery of siRNA, and this research has revealed a need for combination strategies and new formulations. For this reason, a combinatorial synthesis of more than a thousand chemically diverse core-shell nanoparticles with cationic cores and variable shells was performed and these were tested for intracellular siRNA and pDNA delivery.[16] This study highlighted a certain design criteria for future nanoparticle development. In general, nanoparticle delivery tools (lipid- and polymer-based) also require targeting moieties, such as antibodies, aptamers and small peptides for directed delivery and improved specificity.[11, 12]

As to the second challenge, sustained release of siRNA is highly desirable for many therapeutic applications, for example, where frequent siRNA injections are painful or high doses of intracellular siRNA levels are associated with toxicity.[17, 18] Nanoparticles have already been engineered to act as a depot, resulting in slow, sustained, and targeted release of drugs, including siRNA.[19-23] The majority of biodegradable formulations that have provided sustained release of siRNA have employed polymeric materials in which siRNA is incorporated in a polymer core.[19-23] Alternatively, a modern class of biodegradable solid lipid nanoparticles (SLNPs), prepared from lipids that remain solid at body temperature, have been developed.[24-27] SLNPs have been used to incorporate various drugs, as well as imaging agents with the benefits of using physiological and nontoxic lipids.[24, 27-30] Despite its many advantages, this type of nanoparticle remains largely unexplored for sustained oligonucleotide delivery. The hydrophobic nature of SLNPs impedes efficient loading of hydrophilic drugs, such as oligonucleotides. For protein- and peptide-loaded SLNPs, this challenge has partially been resolved by making peptide-surfactant conjugates prior loading into SLNPs, which results in prolonged payload release.[28, 29]

In this paper we make a step toward using SLNPs for sustained siRNA delivery. We show that SLNPs can be loaded with siRNA by using a hydrophobic ion pairing (HIP) approach. The HIP we use consists of a tight complex of siRNA and a cationic lipid (DOTAP), allowing for efficient siRNA incorporation into the SLPN core. We demonstrate that prepared nanoparticles provide sustained release of siRNA in vitro and in vivo over a period of 10-13 days, with retained functionality.

Results and Discussion

Various solid lipids (such as tristearin, trilaurin, trimyristin, palmitic or stearic acids) and stabilizers (such as phospholipids, Pluronic F68 or Tween 80) have been employed to form SLNPs.[24, 27, 28] A number of reports describe applications of SLNPs for siRNA or DNA delivery.[31-34] In these studies, however, SLNPs are usually formed prior to binding of the oligonucleotides on the surface of the nanoparticle (NP), with no sustained in vivo release reported.[31-34] Solid lipids are hydrophobic molecules, which have little interaction with charged molecular species, whereas siRNAs are hydrophilic, negatively charged molecules. Such a difference in the properties between siRNA and solid lipids makes it difficult to incorporate oligonucleotides in the core of the SLNPs.

One way to overcome a challenge of loading SLNPs with oligonucleotides is to use a hydrophobic ion pairing (HIP) approach.[19, 20, 35] HIP is a technique in which a drug-surfactant complex is formed. This complex increases the lipophilicity of the drug, and allows for incorporation of the drug in the lipid core of SLNP. In this study we use a modified Bligh-Dyer method to form an HIP.[36] Briefly, a single-phase solution, consisting of chloroform/methanol/water (CHF/MeOH/$H_2O$, in the volume ratio of 1:2.2:1) is prepared. This solution contained siRNA and a cationic lipid DOTAP in a 1:1 charge ratio, i.e., one DOTAP molecule per phosphate group on the siRNA. In this mixture, DOTAP binds to siRNA and forms a HIP. The siRNA/DOTAP complex is tightly held together by electrostatic interaction between the negatively charged phoshodiester backbone and the positively charged DOTAP headgroup, while the DOTAP hydrophobic domains facilitate efficient encapsulation of the siRNA/DOTAP complex in the lipid nanoparticle.[20]

To prepare SLNPs, we use a nanoprecipitation/solvent displacement technique, which is similar to production of polymer nanoparticles, and which has been used for preparing SLNPs.[33, 34, 37, 38] First, lipids such as lecithin and DSPE-PEG were dissolved in a water/methanol ($H_2O$/MeOH) receiver solution and pre-heated to 65° C. under gentle stirring. After the temperature was decreased to 35-40° C., the siRNA/DOTAP complex in the CHF/MeOH/$H_2O$ was added to the receiver solution (FIG. 1a-c, Feed solution 1). Next, a CHF solution of solid lipids was added to the receiver solution (FIG. 1a-c, Feed solution 2).

Alternatively, the siRNA/DOTAP complex was extracted in CHF solution by phase separation and then dried until the CHF and water residues are evaporated. The dried siRNA/DOTAP complex was easily solubilized by CHF, mixed with solid lipids and then added to the receiver solution (FIGS. 1b and 1d).

After all the ingredients were added to the receiver solution, organic solvents were allowed to evaporate for 4-12 hours under stirring, leading to nanoparticle precipitation. Occasionally, the solution was sonicated for 30 seconds to reduce nanoparticle agglomeration. Finally, the remaining organic solvents were removed by rotary evaporation, along with some of the water in order to obtain the desired final volume.

During the precipitation process, phospholipids were allowed to self-assemble on the nanoparticle surface with the hydrophobic hydrocarbon chains facing the solid lipid core, with the hydrophilic lipid head-groups and PEG moieties facing the aqueous environment (FIG. 1e). Coating SLNPs and polymer NPs with phospholipids and PEGylated lipids is a common approach,[30, 37] which has several advantages. Lipids and PEG moieties on the nanoparticle surface are used to stabilize nanoparticle dispersion; moreover, PEGylated NPs have prolonged circulation times in vivo, as well as reduced immunogenicity.[39]

Figure 2:
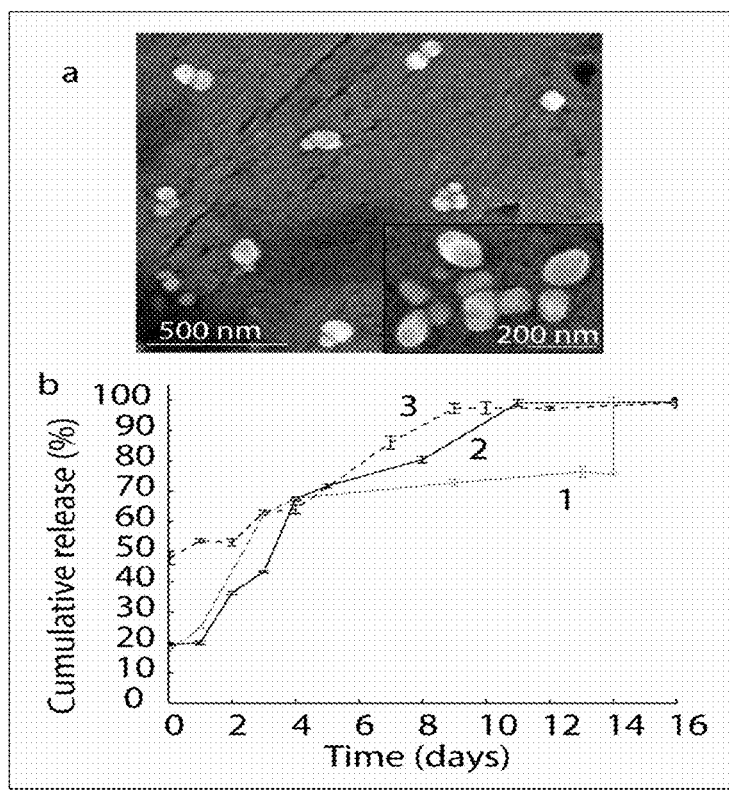
FIG. 2(a) illustrates SEM images of SLNPs.
FIG. 2(b) Cumulative release rate of siRNA from SLNPs. Line 1, 5.5 wt % of K6a_513a. 12 siRNA; during the NP preparation the receiver solution contained an additional 0.5 wt % of PF 68, which had no effect on NP size. Line 2, 4.4 wt % of Accell CBL3 siRNA, and line 3, 4.8 wt % of K6a_513a. 12 siRNA.

The resulting SLNPs have diameters of ~150 nm as determined by scanning electron microscopy (SEM, FIG. 2a.) Dynamic light scattering measurements indicate some degree of agglomeration, with the main peak size ranging from 255 to 615 nm. The zeta potential of the nanoparticles is −20 mV in dilute phosphate solution (PBS) buffer.

Sustained release of siRNA from SLNPs in PBS (pH 7.4) containing surfactant Pluronic F68 (1 wt %) was determined by measuring the concentration of siRNA over time using the fluorescent dye SYBRGold (FIG. 2b), as described in the Experimental Section. The surfactant PF 68 was added to help disperse the SLNPs. In FIG. 2b, SLNPs corresponding to lines 1 and 2 have been prepared according to the scheme shown in FIG. 1a-c with the DSPE-PEG/lecithin/tristearin mass ratio 0.1:0.2:1. The siRNA encapsulation ratio in line 1 is 5.5 wt %, and 4.4 wt % in line 2.

The initial siRNA burst (i.e., the amount of unencapsulated siRNA) is 17% and 22% in curves 1 and 2, respectively. We also observed that a certain amount of siRNA remained unreleased from SLNPs. To determine this amount, we dried the remaining nanoparticles and dissolved them in CHF solution. Next, a known amount of water was added to CHF, and siRNA was extracted into the aqueous phase.

The siRNA concentration in water was measured as described above. The last data point in line 1 shows an example of such a measurement. Despite the observation that some siRNA remains unreleased in vitro, the in vivo degradation of SLNPs and release of siRNA may be facilitated by lipases present in a physiological milieu.[26] SLNPs with the release rate shown in FIG. 2b, line 3, were prepared by combining the siRNA/DOTAP complex and solid lipids in the same CHF solution with the mass ratio of DSPE-PEG/lecithin/tristearin of 0.2:0.5:1 and an siRNA encapsulation ratio of 4.8 wt %. Such a nanoparticle preparation gives a higher initial burst of siRNA (up to 50%). For in vivo testing, we used the NP preparation scheme shown in FIG. 1a-c.

Figure 3:
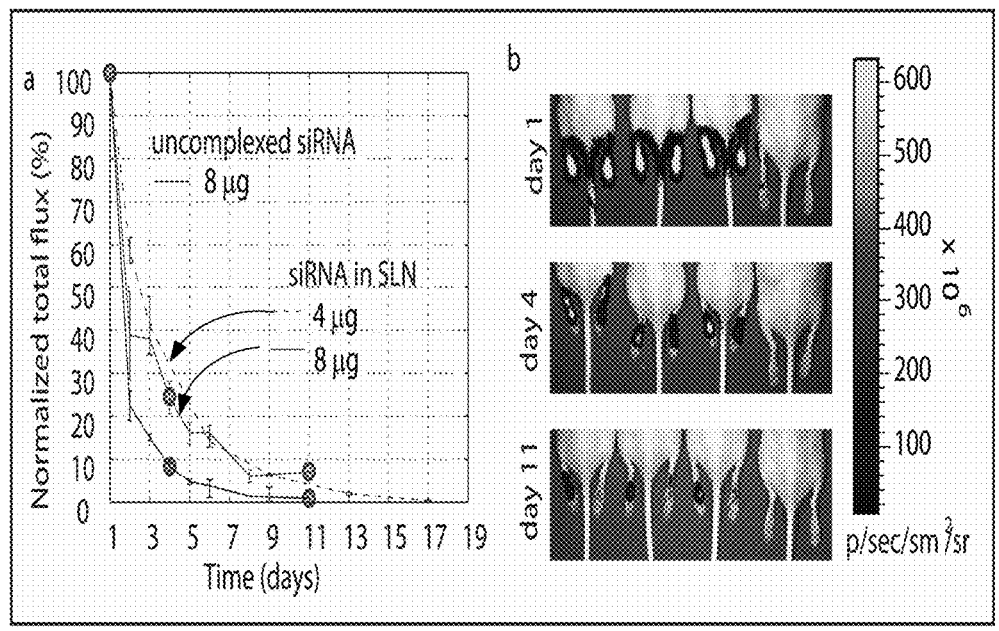
FIG. 3(a) illustrates the normalized total flux versus time shows in vivo release of unencapsulated siGLO Red (black solid line) and siGLO Red encapsulated in SLNPs (red lines). Solid lines were obtained from a cohort of mice (n=3) by injecting siGLO Red SLNPs into the left paws, and unencapsulated siGLO Red into right paws FIG. 3(b) siGLO Red fluorescence signal collected from mouse paws injected with 8 g of siGLO Red. Images correspond to the data points from the solid red and black lines in FIG. 3a, which are indicated with circles. The mouse on the right is a negative control with no siRNA or SLNP injected. Scale bar units are photons per second per $cm^2$ per steradian.

To determine the in vivo release rate of siRNA, we injected a solution of SLNPs containing a fluorescently labelled siRNA mimic, (siGLO Red) as well as unencapsulated siGLO Red at intradermal (ID) sites in footpads of mice. Intradermal injection of the nanoparticles allows for facile in vivo imaging due to the proximity of the SLNPs to the skin surface. In vivo red fluorescence signal was measured using an IVIS 200 imaging system as described in the Experimental Section. SLNPs were prepared with 5 wt % and 4.4 wt % of siGLO Red and a total dose of 4 μg and 8 μg—dashed and solid red lines in FIG. 3a, respectively. Each dose was administered to a different group of mice. The lecithin/DSPE-PEG/tristearin mass ratio was 0.5:0.1:1 for the dashed line, and 0.2:0.1:1 for the solid line. Despite the slight difference in SLNP formulation, the in vivo release curves of siGLO Red look similar. FIG. 3 shows the decrease in fluorescence over time, with a faster decrease in signal for unencapsulated siGLO Red. During the first 24 h, the fluorescence intensity of unencapsulated siRNA decreases by 80%, versus 42-60% for siGLO Red SLNPs, as shown in FIG. 3a. Changes in fluorescence intensity for unencapsulated siRNA mirror our previous results, where doses of 2 and 10 μg in 50 μL of unencapsulated siRNA were intradermally injected into the mice footpads.[20] During the following 13 days (d) we observed a rapid decrease in fluorescence intensity for unencapsulated siGLO Red versus sustained release of siGLO Red from SLNPs. The observed in vivo dynamics mimic the in vitro release of siRNA (FIG. 2b) in PBS solution.

In the in vitro experiments, siRNAs were released over the period of 9-10 d, and in the in vivo experiments, the siGLO Red signal decreased over the period of 10-13 d. FIG. 3b shows images of mouse paws with siGLO Red fluorescence collected on day 1 (immediately following the initial injection), day 4 and day 11 (left paws: siGLO Red SLNPs; right paws: unencapsulated siGLO Red). The image, taken on day 1 in FIG. 3b corresponds to the data point marked with the circle at day 1 in FIG. 3a. Both paws in FIG. 3b at day 1 show high fluorescence signal. Images, taken on day 4 and 11 in FIG. 3b correspond to the data points marked with the circles on days 4 and 11 in FIG. 3a (red solid line is for siGLO Red SLNP, and black line is for unencapsulated siGLO Red). The observed difference in fluorescence intensities between unencapsulated siGLO Red and siGLO Red SLNPs confirms the sustained release of siGLO Red from SLNPs.

Figure 4:
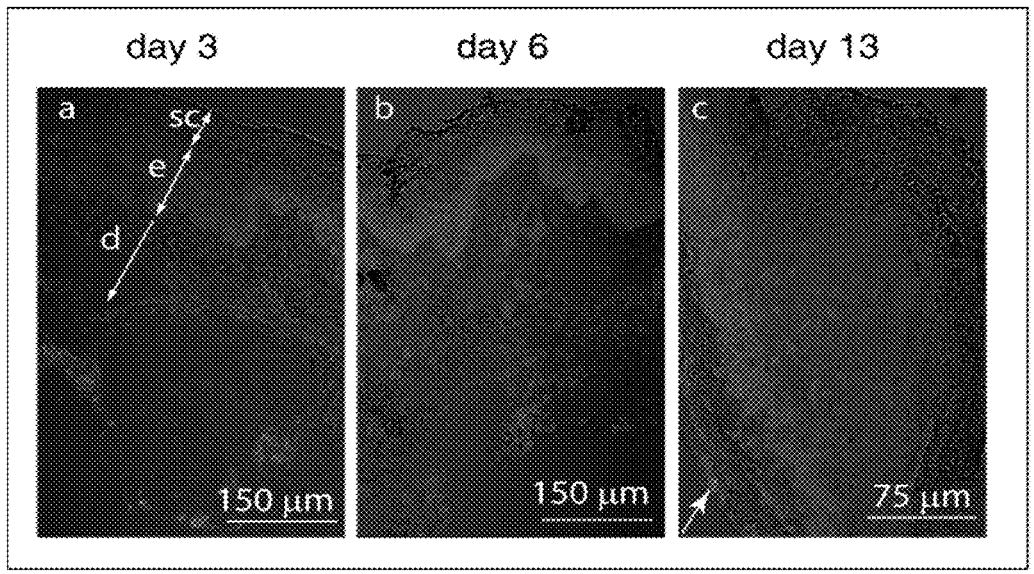
FIG. 4 illustrates fluorescence microscopy of skin sections prepared from mice treated with siGLO Red nanoparticles.

Additionally, confocal fluorescence microscopy was used to analyze the distribution of siGLO Red SLNPs in frozen skin sections prepared from footpads obtained from a separate group of mice that were treated in similar fashion to those shown in FIG. 3. Fluorescence microscopy (FIG. 4) confirmed the presence of the siGLO Red SLNPs in the skin sections in the time period up to 13 d. On day 3, siRNA signal is detected in both the epidermis and dermis (FIG. 4a). On day 6, the majority of siRNA is observed in the dermis (FIG. 4b). Similarly, on day 13, the remaining siGLO Red signal is in the dermis (FIG. 4c).

Figure 5:
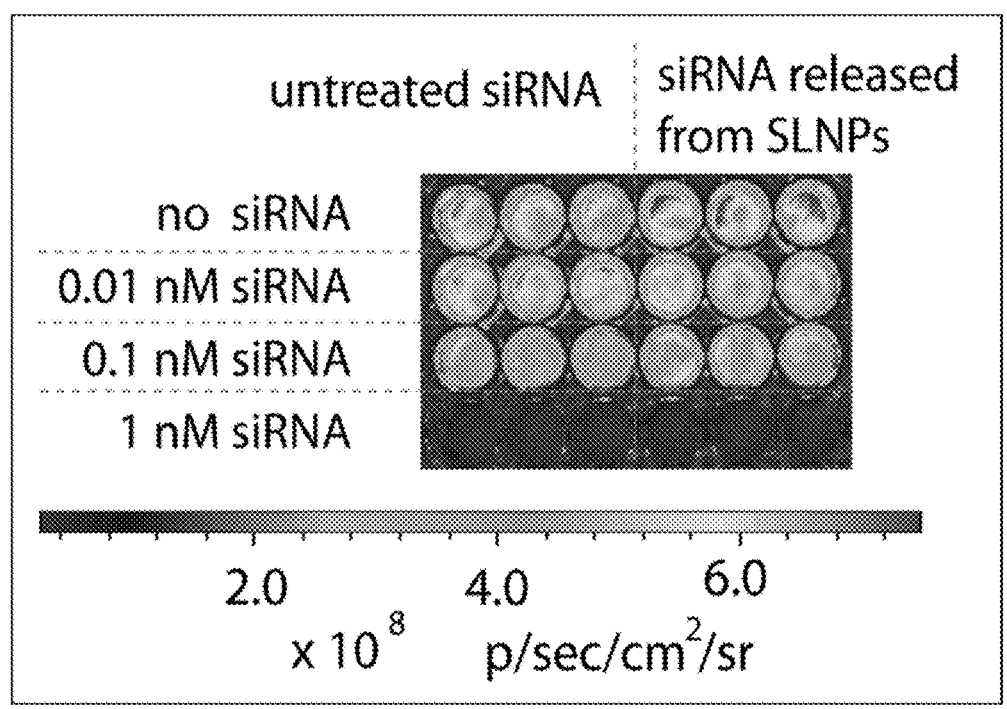
FIG. 5 illustrates the siRNA recovered from SLNPs has similar activity to unformulated input siRNA. Human 293FT cells were co-transfected in triplicate with pTD138 (a plasmid that expresses click beetle luciferase $CBL^{17}$) and 0.01 to 1 nM unprocessed siRNA or siRNA released from SLNPs siRNAs as indicated. Luciferin was added 48 h post-transfection and bioluminescence was visualized by using a Luminal I imaging system (Xenogen product from Caliper LifeSciences).

In order to verify that siRNA released from SLNPs retains functional activity, siRNA released from SLNPs was collected after a 7 day incubation at 37° C. and analyzed for functional activity in transfected human 293FT cells. The results show that siRNA packaged in SLNPs retain the same functional activity as the original input siRNA (FIG. 5).

Conclusion

In summary, solid lipid nanoparticles were developed that allow for sustained in vivo siRNA delivery. Nanoparticles were loaded with siRNA molecules by using hydrophobic ion pairing approach in which functional siRNA activity was retained. Ion pairs consisted of siRNA and cationic lipid DOTAP, which allowed for efficient siRNA incorporation in the hydrophobic core of SLNP. The in vivo experiments demonstrate that SLNPs provide sustained release of siRNA in the period 10-13 days followed by the intradermal injection of the nanoparticles. SLNPs may act as a sustained release system to prolong in vivo siRNA delivery and thus may control gene expression over time. Additionally, SLNPs provide an advantage of being prepared from physiological lipids with excellent biocompatibility, minimal toxicity, and they are less costly comparing to polymeric carriers.

Experimental

Materials:
Analytical grade methanol, chloroform, molecular grade RNAse-free water and PBS buffer (pH 7.4) were obtained from Fisher Scientific (Pittsburgh, Pa.). Tristearin was from Sigma Aldrich (St. Louis, Mo.), DOTAP (1,2-dioleoyl-3-trimethylammonium-propane), soybean lecithin (L-α-phosphatidylcholine), DSPE-PEG (1,2-dioleoyl-sn-glycero-3-phosphoethanolamine-N-(methoxy(polyethylene glycol)-2000) were from Avanti Polar Lipids (Alabaster, Ala.), and SYBR®Gold from Invitrogen (Carlsbad, Calif.). The K6a_513a.12 siRNA[40] and Accell CBL3 siRNA for the in vitro release study, and siGLO Red (DY-547) for the in vivo experiments were provided by Thermo Fisher Scientific, Dharmacon Products (Lafayette, Colo.).

Synthesis of the Nanoparticles:
Lecithin and DSPE-PEG, dissolved in a 1:2 water/methanol solution with addition of 0.5% of 1-butanol as a co-surfactant (typical volume 9-18 mL with lipid concentration 15-100 μg/mL), were pre-heated to 65° C. under gentle stirring (receiver solution). After the temperature was decreased to 35-40° C., the siRNA/DOTAP complex in the CHF/MeOH/$H_2O$ solution (total volume 840 μL) was added to the receiver solution. After that tristearin (1 mg), dissolved in CHF at the concentration of 10 mg/mL was added to the receiver solution. Alternatively, siRNA/DOTAP was extracted in CHF solution by phase separation, i.e., addition of equal amounts of water and CHF. The siRNA/DOTAP complex in CHF phase was then dried over a period of 8 h at room temperature until the CHF and water residues are evaporated. The dried siRNA/DOTAP complex was solubilised by CHF and mixed with solid lipids (500 μL of total feed solution) and then added to the receiver solution. siRNA/DOTAP complex can also be stored at −20° C. for further use. The typical mixing mass ratio of siRNA/DOTAP/DSPE-PEG/lecithin/tristearin was 0.1:0.25:0.1-0.2:0.2-0.5:1. Organic solvents were allowed to evaporate for 4-12 h under stirring, leading to nanoparticle precipitation. During the precipitation process, the solution was sonicated for 30 seconds (PC3 Ultrasonics, bath sonicator at a frequency of 50 kHz). The remaining organic solvents were removed by rotary evaporation.

Particle Analysis:
Scanning electron microscope (SEM) images were acquired using an FEI XL30 Sirion SEM with FEG source and EDX detector. Dilute aqueous nanoparticle solution was placed on SEM mount, and water was allowed to evaporate prior SEM imaging. The hydrodynamic diameter and zeta potential of the SLNPs were measured using a Malvern Zetasizer Nano Z590. The zeta potential of the nanoparticles was measured in phosphate-buffered saline solution (PBS, pH 7.4) diluted with water (1:20 dilution).

Release Data:
Sustained release of siRNA (K6a_513a.12 siRNA or Accell CBL3 siRNA) from SLNPs was performed by dispersing SLNPs in PBS solution (1% PF 68) in a typical volume of 10-15 mL. At each time interval 500 μL solution was removed and centrifuged for 5 min at 13 k rpm to collect NPs. The remaining SLNP solution was either replenished with a given amount of PBS solution or directly placed at 37° C. for further incubation. 50 μL SYBR®Gold (1/500 dilution) was added to triplicate samples of 100 μL siRNA solution to measure fluorescence intensity, which was compared to a standard concentration curve. The encapsulation ratio was defined as 100*(siRNA mass)/(total mass of the components used in the NP preparation). For a typical NP preparation, on average 50% of the initial amount of siRNA was detected by the release measurements, which indicates 50% encapsulation efficiency. This amount was defined as the maximum (100%) of cumulative release in FIG. 2b. Each error bar represents the standard error.

In Vivo Imaging:

Mouse paws (CD1 mice, Charles River, Hollister, Calif.) were imaged in an IVIS 200 imaging system (Xenogen product from Caliper LifeSciences) using the DsRed filter set (excitation at 460-490 nm and 500-550 nm; emissions at 575-650 nm). LivingImage software (Caliper LifeSciences) was used to quantify the resulting light emission, written as an overlay on Igor image analysis software (WaveMetrics, Inc.). DsRed background was subtracted and raw values were reported as photons per second per $cm^2$ per steradian. For each siRNA dose (injection volume is 20-30 µL), a group of three mice was used for in vivo imaging. Error bars in FIG. 3a are standard errors.

Tissue Preparation and Imaging:

Skin sections were prepared by removing footpad skin from euthanized mice. Skin sections were embedded in O.C.T. (Tissue-Tek®, Torrance, Calif.) compound and frozen directly on dry ice. Skin cross sections were prepared, stained with Syto-62 fluorescent dye for nuclear and cytoplasmic staining, and mounted with Hydromount™ (National Diagnostic).

Microscopic visualization of tissue sections was performed using an upright Leica TCS SP2 AOBS confocal laser scanning microscope (Leica Microsystems, Wetzlar, Germany) equipped with HC PL FLUOTAR 20× air objective. The 543-nm line of a He/Ne laser was used for excitation of siGLO RED, and the emission was collected by a photomultiplier tube at 565-623 nm. The 633-nm line of a He/Ne laser was used for excitation of Syto-62, and the emission was collected by a photomultiplier tube at 660-750 nm.

In Vitro Assay:

Functional activity of CBL3 siRNA released from the SLNPs in PBS solution was compared to the untreated siRNA. SLNPs loaded with Accell CBL3 siRNA were prepared with an encapsulation ratio of 4.3 wt % (initial siRNA mass was 400 µg). Nanoparticles were dispersed in 2 ml of PBS (pH 7.4) and were incubated for 7 days at 37° C. to allow siRNA release. On day 7, the nanoparticle solution was filtered with 0.1 µm centrifugal filter device (10 min at 13,200 rpm). After that, the nanoparticle suspension was concentrated with Amicon Ultra filter devices with the molecular weight cutoff 3 kDA. This solution was further centrifuged for 10 min at 13,200 rpm to allow any NPs to settle. The top aqueous siRNA solution was collected and used for the in vitro study.

siRNA functional activity was determined as described previously[40] with slight modifications. Briefly, 293FT cells were co-transfected (in triplicate) with a mixture of 40 ng pTD138 expression plasmid[17], 360 ng pUC19 (as nucleic acid "filler"), Accell CBL3 siRNA (final concentration 0.01 to 1 nM per transfection) and K6a_513a.12 siRNA (to give a final total siRNA concentration of 1 nM per transfection) diluted with 25 µL in optiMEM medium (Invitrogen). One microliter of Lipofectamine 2000 was diluted in 25 µL of optiMEM medium, added to the nucleic acid mixture and incubated for 20 min at room temperature, prior to addition to the plated cells. After transfection (48 h), luciferin substrate (50 µL of a 3 mg/mL solution) was added and the light emitted was visualized using the Xenogen Lumina II in vivo imaging system.

References, which are incorporated herein by reference

1. Juliano, R.; Bauman, J.; Kang, H.; Ming, X., Biological Barriers to Therapy with Antisense and siRNA Oligonucleotides. *Mol. Pharm.* 2009, 6, 686-695.
2. Gonzalez-Gonzalez, E.; Speaker, T. J.; Hickerson, R. P.; Spitler, R.; Flores, M. A.; Leake, D.; Contag, C. H.; Kaspar, R. L., Silencing of Reporter Gene Expression in Skin Using siRNAs and Expression of Plasmid DNA Delivered by a Soluble Protrusion Array Device (PAD). *Mol. Ther.* 2010, 18, 1667-1674.
3. Li, C. X.; Parker, A.; Menocal, E.; Xiang, S. L.; Borodyansky, L.; Fruehauf, J. H., Delivery of RNA Interference. *Cell Cycle.* 2006, 5, 2103-2109.
4. Tokatlian, T.; Segura, T., siRNA Applications in Nanomedicine. *Wiley Interdiscip. Rev.: Nanomed. Nanobiotechnol.* 2010, 2, 305-315.
5. Hickerson, R. P.; Vlassov, A. V.; Wang, Q.; Leake, D.; Ilves, H.; Gonzalez-Gonzalez, E.; Contag, C. H.; Johnston, B. H.; Kaspar, R. L., Stability Study of Unmodified siRNA and Relevance to Clinical Use. *Oligonucleotides.* 2008, 18, 345-354.
6. Dykxhoorn, D. M.; Lieberman, J., Knocking Down Disease with siRNAs. *Cell.* 2006, 126, 231-235.
7. Li, W. J.; Szoka, F. C., Lipid-Based Nanoparticles for Nucleic Acid Delivery. *Pharm. Res.* 2007, 24, 438-449.
8. Whitehead, K. A.; Langer, R.; Anderson, D. G., Knocking Down Barriers: Advances in siRNA Delivery. *Nat. Rev. Drug Discovery.* 2009, 9, 412-412.
9. Kornek, M.; Lukacs-Kornek, V.; Limmer, A.; Raskopf, E.; Becker, U.; Kloeckner, M.; Sauerbruch, T.; Schmitz, V., 1,2-Dioleoyl-3-Trimethylammonium-Propane (DOTAP)-Formulated, Immune-Stimulatory Vascular Endothelial Growth Factor a Small Interfering RNA (siRNA) Increases Antitumoral Efficacy in Murine Orthotopic Hepatocellular. *Mol. Med.* 2008, 14, 365-373.
10. Urban-Klein, B.; Werth, S.; Abuharbeid, S.; Czubayko, F.; Aigner, A., RNAi-Mediated Gene-Targeting Through Systemic Application of Polyethylenimine (PEI)-Complexed siRNA in Vivo. *Gene Ther.* 2005, 12, 461-466.
11. Davis, M. E.; Zuckerman, J. E.; Choi, C. H. J.; Seligson, D.; Tolcher, A.; Alabi, C. A.; Yen, Y.; Heidel, J. D.; Ribas, A., Evidence of RNAi in Humans from Systemically Administered siRNA via Targeted Nanoparticles. *Nature (London, U.K).* 2010, 464, 1067-1070.
12. Guo, P. X.; Coban, O.; Snead, N. M.; Trebley, J.; Hoeprich, S.; Guo, S. C.; Shu, Y., Engineering RNA for Targeted siRNA Delivery and Medical Application. *Adv. Drug Delivery Rev.* 2010, 62, 650-666.
13. Tsutsumi, T.; Hirayama, F.; Uekama, K.; Arima, H., Potential Use of Polyamidoamine Dendrimer/Alpha-Cyclodextrin Conjugate (Generation 3, G3) as a Novel Carrier for Short Hairpin RNA-Expressing Plasmid DNA. *J. Pharm. Sci.* 2008, 97, 3022-3034.
14. Han, H. D.; Mangala, L. S.; Lee, J. W.; Shahzad, M. M. K.; Kim, H. S.; Shen, D. Y.; Nam, E. J.; Mora, E. M.; Stone, R. L.; Lu, C. H.; et al., Targeted Gene Silencing Using RGD-Labeled Chitosan Nanoparticles. *Clin. Cancer Res.* 2010, 16, 3910-3922.
15. Woodrow, K. A.; Cu, Y.; Booth, C. J.; Saucier-Sawyer, J. K.; Wood, M. J.; Saltzman, W. M., Intravaginal Gene Silencing Using Biodegradable Polymer Nanoparticles Densely Loaded with Small-Interfering RNA. *Nat. Mater.* 2009, 8, 526-533.
16. Siegwart, D. J.; Whitehead, K. A.; Nuhn, L.; Sahay, G.; Cheng, H.; Jiang, S.; Ma, M. L.; Lytton-Jean, A.; Vegas, A.; Fenton, P.; et al., Combinatorial Synthesis of Chemically Diverse Core-Shell Nanoparticles for Intracellular Delivery. *Proc. Natl. Acad. Sci. U.S.A.* 2011, 108, 12996-13001.
17. Gonzalez-Gonzalez, E.; Ra, H.; Hickerson, R. P.; Wang, Q.; Piyawattanametha, W.; Mandella, M. J.; Kino, G. S.; Leake, D.; Avilion, A. A.; Solgaard, O.; Doyle, T. C.; et al., siRNA Silencing of Keratinocyte-Specific GFP Expression in a Transgenic Mouse Skin Model. *Gene Ther.* 2009, 16, 963-972.
18. Judge, A.; Maclachlan, I., Overcoming the Innate Immune Response to Small Interfering RNA. *Hum. Gene Ther.* 2008, 19, 111-124.
19. Lee, S.; Yang, S. C.; Kao, C.-Y.; Pierce, R. H.; Murthy, N., Solid Polymeric Microparticles Enhance the Delivery of siRNA to Macrophages in Vivo. *Nucleic Acids Res.* 2009, 37, e145.
20. Jacobson, G. B.; Gonzalez-Gonzalez, E.; Spitler, R.; Shinde, R.; Leake, D.; Kaspar, R. L.; Contag, C. H.; Zare, R. N., Biodegradable Nanoparticles With Sustained Release of Functional siRNA in Skin. *J. Pharm. Sci.* 2010, 99, 4261-4266.
21. Krebs, M. D.; Jeon, O.; Alsberg, E., Localized and Sustained Delivery of Silencing RNA from Macroscopic Biopolymer Hydrogels. *J. Am. Chem. Soc.* 2009, 131, 9204-9206.
22. Patil, Y.; Panyam, J., Polymeric Nanoparticles for siRNA Delivery and Gene Silencing. *Int. J. Pharm.* 2009, 367, 195-203.
23. Shi, J.; Xiao, Z.; Votruba, A. R.; Vilos, C.; Farokhzad, O. C., Differentially Charged Hollow Core/Shell Lipid-Polymer-Lipid Hybrid Nanoparticles for Small Interfering RNA Delivery. *Angew. Chem., Int. Ed. Engl.* 2011, 50, 7027-31.
24. Mehnert, W.; Mader, K., Solid Lipid Nanoparticles—Production, Characterization and Applications. *Adv. Drug Delivery Rev.* 2001, 47, 165-196.
25. Jain, A.; Agarwal, A.; Majumder, S.; Lariya, N.; Khaya, A.; Agrawal, H.; Majumdar, S.; Agrawal, G. P., Mannosylated Solid Lipid Nanoparticles as Vectors for Site-Specific Delivery of an Anti-Cancer Drug. *J. Controlled Release.* 2010, 148, 359-367.
26. Xue, H. Y.; Wong, H. L., Tailoring Nanostructured Solid-Lipid Carriers for Time-Controlled Intracellular siRNA Kinetics to Sustain RNAi-Mediated Chemosensitizationd. *Biomaterials.* 2011, 32, 2662-2672.
27. Wissing, S. A.; Kayser, O.; Muller, R. H., Solid Lipid Nanoparticles for Parenteral Drug Delivery. *Advanced Drug Delivery Reviews.* 2004, 56, 1257-1272.
28. Almelda, A. J.; Souto, E., Solid Lipid Nanoparticles as a Drug Delivery System for Peptides and Proteins. *Adv. Drug Delivery Rev.* 2007, 59, 478-490.
29. Gallarate, M.; Battaglia, L.; Peira, E.; Trotta, M., Peptide-Loaded Solid Lipid Nanoparticles Prepared through Coacervation Technique. *Int. J. Chem. Eng.* 2011, 2011, 1-6.
30. Andreozzi, E.; Seo, J. W.; Ferrara, K.; Louie, A., Novel Method to Label Solid Lipid Nanoparticles with Cu-64 for Positron Emission Tomography Imaging. *Bioconjugate Chem.* 2011, 22, 808-818.
31. Kim, H. R.; Kim, I. K.; Bae, K. H.; Lee, S. H.; Lee, Y.; Park, T. G., Cationic Solid Lipid Nanoparticles Reconstituted from Low Density Lipoprotein Components for Delivery of siRNA. *Mol. Pharmaceutics.* 2008, 5, 622-631.
32. Pedersen, N.; Hansen, S.; Heydenreich, A. V.; Kristensen, H. G.; Poulsen, H. S., Solid Lipid Nanoparticles Can Effectively Bind DNA, Streptavidin and Biotinylated Ligands. *Eur. J. Pharm. Biopharm.* 2006, 62, 155-162.
33. Yu, W.; Liu, C.; Liu, Y.; Zhang, N.; Xu, W., Mannan-Modified Solid Lipid Nanoparticles for Targeted Gene Delivery to Alveolar Macrophages. *Pharm. Res.* 2010, 27, 1584-1596.
34. Yu, W.; Liu, C.; Ye, J.; Zou, W.; Zhang, N.; Xu, W., Novel Cationic SLN Containing a Synthesized Single-Tailed Lipid as a Modifier for Gene Delivery. *Nanotechnology.* 2009, 20, 215102.
35. Patel, M. M.; Zeles, M. G.; Manning, M. C.; Randolph, T. W.; Anchordoquy, T. J., Degradation Kinetics of High Molecular Weight Poly (L-lactide) Microspheres and Release Mechanism of Lipid: DNA Complexes. *J. Pharm. Sci.* 2004, 93, 2573-2584.
36. Bligh, E. G.; Dyer, W. J., A Rapid Method of Total Lipid Extraction and Purification. *Can. J. Biochem. Physiol.* 1959, 37, 911-917.
37. Chan, J. M.; Zhang, L. F.; Yuet, K. P.; Liao, G.; Rhee, J. W.; Langer, R.; Farokhzad, O. C., PLGA-lecithin-PEG Core-Shell Nanoparticles for Controlled Drug Delivery. *Biomaterials.* 2009, 30, 1627-1634.
38. Zhang, S.; Yun, J.; Shen, S.; Chen, Z.; Yao, K.; Chen, J.; Chen, B., Formation of Solid Lipid Nanoparticles in a Microchannel System with a Cross-Shaped Junction. *Chem. Eng. Sci.* 2008, 63, 5600-5605.
39. Alexis, F.; Pridgen, E.; Molnar, L. K.; Farokhzad, O. C., Factors Affecting the Clearance and Biodistribution of Polymeric Nanoparticles. *Mol. Pharmaceutics.* 2008, 5, 505-515.
40. Hickerson, R. P.; Smith, F. J. D.; Reeves, R. E.; Contag, C. H.; Leake, D.; Leachman, S. A.; Milstone, L. M.; McLean, W. H. I.; Kaspar, R. L., Single-Nucleotide-Specific siRNA Targeting in a Dominant-Negative Skin Model. *J. Invest. Dermatol.* 2008, 128, 594-605.
41. Ge, J.; Jacobson, G. B.; Lobovkina, T.; Holmberg, K.; Zare, R. N., Sustained Release of Nucleic Acids from Polymeric Nanoparticles Using Microemulsion Precipitation in Supercritical Carbon Dioxide. *Chem. Commun.* (Cambridge, U. K.). 2010, 46, 9034-6.

Example 2

Background

Nanoparticle drug delivery systems allow for incorporating and controlling release of therapeutic payloads. In recent years, a considerable amount of research has been devoted to production of various types of biodegradable nanoparticles for drug delivery to acquire good biological tolerance.[1-4] In the diversity of the drug nanocarriers, the nanoemulsion systems are considered to be very promising.[4-6] Generally, nanoemulsion consists of oil 20-500 nm droplets, which are stabilized by an appropriate surfactant and dispersed in aqueous media. Nanoemulsions have been used for ocular, transdermal and intravenous delivery of lipophilic drugs.[4,5] Recently, a multifunctional platform for theranostic applications based on oil-in-water nanoemulsion has been developed.[3,7] Despite the variety of biodegradable components that are used for nanoparticle preparations, there is a growing concern associated with the biological tolerance of these materials.[8-10] Here we suggest a novel type of oil-in-water nanoemulsion system that will be prepared from lipids extracted from human adipose tissue (HAT). These lipids will provide an ideal natural construction material for nanoemulsions. Human adipose tissues have already been used for preparing extracellular matrix scaffolds for tissue engineering and have shown a great potential in that area.[11-14] Adipose tissues can easily be obtained by a common surgical procedure, which originally was intended to remove unwanted tissue. Adipose tissues are rich in lipid content, and a small tissue sample will provide enough material for many nanoemulsion preparations.

As a drug of interest, we have chosen small interfering RNA (siRNA), which is a highly potent compound in gene-based therapy owing to its ability to silence selected genes. We suggest using a hydrophobic ion pairing (HIP) approach to load a nanoemulsion with siRNA. HIP consists of an siRNA molecule and a cationic surfactant tightly bound together by electrostatic interaction. HIP allows for incorporating siRNA in the hydrophobic core of a nanoparticle.

We envision that this approach will open the possibility of providing a truly personalized treatment to the patient, where the drug nanocarriers will be formulated from the molecular species extracted from the tissues of the same person.

Extraction of Lipids from Human Adipose Tissue.

Human fat is "an abundant natural resource and a renewable one," Nowadays the prevalence of obesity has been rapidly rising in the United States. This cause a rapid increase in the number of patients undergoing elective liposuction Today liposuction is considered a safe and well-tolerated procedure, where between a few hundred milliliters to several liters of fat can be removed from a patients body without any complications. Following the procedure, the lipoaspirate is normally discarded as medical waste. Given the safety and popularity of liposuction, it seems that the discarded fat can be an ideal lipid source for clinical use.

Lipids can be extracted from the HAT by using the Bligh and Dyer extraction method with modifications.[18] Briefly, a sample of HAT can be first washed (optionally) with distilled water to remove blood content. After that, to a tissue sample in water, chloroform is added with the volume equal to the volume of water, following by addition of methanol with the volume 2.2 times of the water volume to obtain a single phase solution. This solution can be vortexed for several seconds or minutes, following by addition of equal amount of water and chloroform to achieve phase separation. As a result, lipids are expected to be extracted to the chloroform phase, and water-methanol solution can be discarded. Optionally, a phase separation step can be avoided if lipids phase-separate directly in a water-methanol-chloroform solution. In this case, lipid phase can be collected, and (optionally) an equal amount of water and chloroform can be added to it in order to repeat phase separation. Collected lipids, dissolved in chloroform phase are rotary evaporated to remove organic solvent. Obtained lipids can be used to prepare the nanoemulsion directly, or they can be stored in the freezer for further use.

Nanoemulsion Preparation.

Nanoemulsion, prepared form lipids extracted from HAT, can be formed by adding dropwise organic phase solution (e.g. chloroform) containing lipids extracted from HAT and surfactants (e.g. lecithin and other lipids or surfactants) to a water-ethanol solution containing nonionic surfactant (e.g. PF 68). Solvents are allowed to evaporate for 1-3 hours or more under stirring condition, following by rotary evaporation to remove the remaining organic solvent. Alternatively, crude emulsion is first formed by a similar procedure. Crude emulsion can be converted to a nanoemulsion either by using probe sonication or by filtering the emulsion through a nanoporous membrane with a given pore size (typically 50-400 nm).

Loading the Nanoemulsion with siRNA.

The HIP approach can be used to load siRNA into the hydrophobic core of nanoemulsion. HIP is a technique in which a drug-surfactant complex is formed. This complex increases the lipophilicity of the drug, and allows for incorporating the drug in the hydrophobic core of the nanoparticle.

Briefly, a single-phase solution, consisting of chloroform/methanol/water ($CHF/MeOH/H_2O$, in the volume ratio of 1:2.2:1) is prepared. To this solution, siRNA and a cationic lipid DOTAP ((1,2-dioleoyl-3-trimethylammonium-propane) are added in a 1:1 charge ratio, i.e., one DOTAP molecule per phosphate group on the siRNA. In this mixture, DOTAP binds to siRNA and forms a HIP. The siRNA/DOTAP complex is extracted in CHF solution by phase separation and then dried until the CHF and water residues are evaporated. After that, the siRNA/DOTAP complex is ready to be used for loading into the nanoemulsion or stored in the freezer for further use. The dried siRNA/DOTAP complex can easily be solubilized by CHF, mixed with lipids extracted from HAT and used for nanoemulsion preparation.

Preliminary Study

Example of HAT Lipids Extraction

Human adipose tissue was obtained from patients undergoing liposuction procedure. Briefly the liposuction was performed by removing adipose tissue from the subcutaneous space by means of blunt-tip hollow cannula attached to a syringe at negative pressure. About 15 ml of adipose tissue was harvested over the superficial gluteal fascia for immediate adipose tissue isolation and the skin incision apposed with nylon sutures. The collected tissue was immediately washed with Sodium chloride solution and transferred to the laboratory for further extraction of the adipose lipids.

In order to extract lipids from HAT, 300 μl of human adipose tissue sample was placed into 2 ml Eppendorf tube, following by addition of 400 μl of chloroform, 400 μl of water and 880 μl of methanol. A clear yellow colored lipid-containing phase was formed at the lower part of the Eppendorf tube. This phase was collected and centrifuged at 13.2 krp for 3 min to remove any residues of the top water-containing phase. To the collected lower oil phase, 200 μl of chloroform and 200 μl of water were added to repeat phase separation. Obtained mixture was shaken and further phase separated by centrifuging at 13.2 krp for 3 min. The top aqueous phase was discarded, and the remaining oil phase was rotary evaporated to remove organic solvent. Collected lipids were stored in the freezer at −20° C. for further use.

Example of Nanoemulsion Preparation and Loading with a Drug Model

In order to demonstrate nanoemulsion preparation from lipids extracted from HAT, and loading nanoemulsion with a drug, we have used fluorescently labelled cholesterol (25-[N-[(7-nitro-2-1,3-benzoxadiazol-4-yl)methyl]amino]-27-norcholesterol, NBD-cholesterol, $\lambda ex=483$ nm, $\lambda em=523$ nm) as a drug model. Nanoemulsion was formed by nanoprecipitation technique, where organic feed solution containing HAT lipids, drug, and surfactants (i.e. lipids) was added dropwise to a receiver solution containing water, ethanol and a surfactant under stirring condition. Receiver solution was prepared by combining 3 ml of water containing 2 wt % of PF 68 and 6 ml of ethanol into a 20 ml glass beaker. In order to prepare feed solution, HAT lipids were thawed, weighted and dissolved in chloroform so that so that the concentration of HAT lipids was 30 mg/ml. Next, the following organic solutions were also used to prepare feed solution: 20 mg/ml of lecithin in ethanol, 2 mg/ml of cholesterol in chloroform, 2.5 mg/ml of DSPE-PEG (2000) in ethanol, and 1 mg/ml of NBD-cholesterol in chloroform. Feed solution was prepared by adding all the lipid ingredients into 600 μl of chloroform so that the final mass of the ingredients was 660 µg of HAT lipids, 340 µg of lecithin, 17 µg of DSPE-PEG (2000), 8 µg of cholesterol and 10 µg of NBD-cholesterol. After adding feed solution dropwise to the receiver solution, the mixture was kept under stirring during four hours, and then rotary evaporated to remove organic solvent along with some water content. Collected nanoemulsion was further kept under stirring over night. Next morning, 300 µl of PBS solution was added to the nanoemulsion so that the final volume of nanoemulsion was 2100 µl.

Cell Transfection with NBD-Loaded Nanoemulsion

To investigate the ability of nanoemulsion to deliver a drug model (i.e., NBD-cholesterol) into cells, we transfected adipose stem cells (ASC) with NDB-loaded nanoemulsion.

Figure 6:
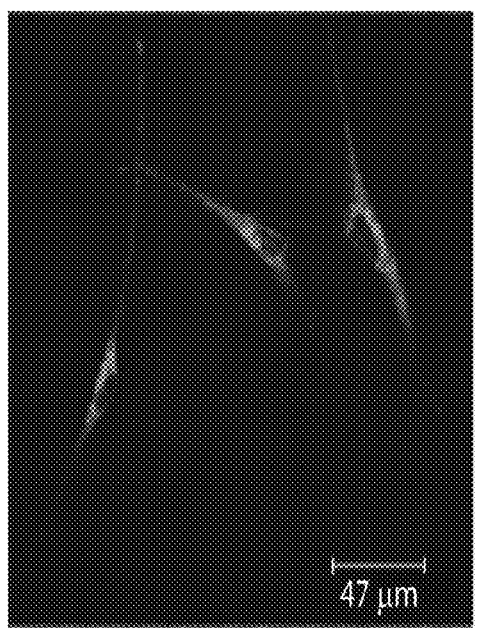
FIG. 6 illustrates cell uptake of nanoemulsion prepared from lipids extracted from HAT and loaded with imaging agent and a drug model, NBD-cholesterol. Cells: adipose-derived human stem cells.

For this experiment we used 6 wells plate format of, seeded with 1×105 mouse adipose stem cells harvested from L2G mice that are expressing GFP signal and Bioluminescences. The ASC were isolated from transgenic L2G FVB mice with β-actin promoter driving firefly luciferase and green fluorescent protein (Fluc-GFP) double fusion reporter gene. The experiment was repeated in triplicates with n=3, where n is the number of wells. The amount of nanoemulsion delivered to each well of cells was 200 µl and left for 4 hours of incubation with the cells at 37 degrees. Following incubation the cells were washed three times with PBS solution and new media were placed into the culture wells. Following this, the cells were observed by confocal laser scanning microscopy, which shows delivery of NBD-cholesterol into cells. FIG. 6 shows confocal laser scanning fluorescence images of human adipose stem cells treated with the nanoemulsion prepared from lipids extracted from HAT and loaded with NBD-cholesterol.

References, each of which is incorporated herein by reference:

1. Panyam, J.; Labhasetwar, V., Biodegradable nanoparticles for drug and gene delivery to cells and tissue. *Advanced Drug Delivery Reviews* 2003, 55, (3), 329-347.
2. Wissing, S. A.; Kayser, O.; Muller, R. H., Solid lipid nanoparticles for parenteral drug delivery. *Advanced Drug Delivery Reviews* 2004, 56, (9), 1257-1272.
3. Gianella, A.; Jarzyna, P. A.; Mani, V.; Ramachandran, S.; Calcagno, C.; Tang, J.; Kann, B.; Dijk, W. J. R.; Thijssen, V. L.; Griffioen, A. W.; Storm, G.; Fayad, Z. A.; Mulder, W. J. M., Multifunctional Nanoemulsion Platform for Imaging Guided Therapy Evaluated in Experimental Cancer. *Acs Nano* 5, (6), 4422-4433.
4. Chen, H. B.; Khemtong, C.; Yang, X. L.; Chang, X. L.; Gao, J. M., Nanonization strategies for poorly water-soluble drugs. *Drug Discovery Today* 16, (7-8), 354-360.
5. Mao, C. W.; Wan, J. L.; Chen, H. B.; Xu, H. B.; Yang, X. L., Emulsifiers' Composition Modulates Venous Irritation of the Nanoemulsions as a Lipophilic and Venous Irritant Drug Delivery System. *Aaps Pharmscitech* 2009, 10, (3), 1058-1064.
6. Tagne, J. B.; Kakumanu, S.; Nicolosi, R. J., Nanoemulsion Preparations of the Anticancer Drug Dacarbazine Significantly Increase Its Efficacy in a Xenograft Mouse Melanoma Model. *Molecular Pharmaceutics* 2008, 5, (6), 1055-1063.
7. Jarzyna, P. A.; Skajaa, T.; Gianella, A.; Cormode, D. P.; Samber, D. D.; Dickson, S. D.; Chen, W.; Griffioen, A. W.; Fayad, Z. A.; Mulder, W. J. M., Iron oxide core oil-in-water emulsions as a multifunctional nanoparticle platform for tumor targeting and imaging. *Biomaterials* 2009, 30, (36), 6947-6954.
8. Lewinski, N.; Colvin, V.; Drezek, R., Cytotoxicity of nanoparticles. *Small* 2008, 4, (1), 26-49.
9. Joralemon, M. J.; McRae, S.; Emrick, T., PEGylated polymers for medicine: from conjugation to self-assembled systems. *Chemical Communications* 46, (9), 1377-1393.
10. Alexis, F.; Pridgen, E.; Molnar, L. K.; Farokhzad, O. C., Factors affecting the clearance and biodistribution of polymeric nanoparticles. *Molecular Pharmaceutics* 2008, 5, (4), 505-515.
11. Choi, J. S.; Kim, B. S.; Kim, J. Y.; Kim, J. D.; Choi, Y. C.; Yang, H. J.; Park, K.; Lee, H. Y.; Cho, Y. W., Decellularized extracellular matrix derived from human adipose tissue as a potential scaffold for allograft tissue engineering. *Journal of Biomedical Materials Research Part A* 97A, (3), 292-299.
12. Choi, J. S.; Yang, H. J.; Kim, B. S.; Kim, J. D.; Lee, S. H.; Lee, E. K.; Park, K.; Cho, Y. W.; Lee, H. Y., Fabrication of Porous Extracellular Matrix Scaffolds from Human Adipose Tissue. *Tissue Engineering Part C—Methods* 16, (3), 387-396.
13. Young, D. A.; Ibrahim, D. O.; Hu, D.; Christman, K. L., Injectable hydrogel scaffold from decellularized human lipoaspirate. *Acta Biomaterialia* 7, (3), 1040-1049.
14. Flynn, L. E., The use of decellularized adipose tissue to provide an inductive microenvironment for the adipogenic differentiation of human adipose-derived stem cells. *Biomaterials* 31, (17), 4715-4724.
15. Bligh, E. G.; Dyer, W. J., A Rapid Method of Total Lipid Extraction and Purification. *Canadian Journal of Biochemistry and Physiology* 1959, 37, (8), 911-917.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to what is being measured. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifiations may be made to the above-described embodiments of the disclosure without departing substantially from the spirit and principles of the disclosure. All such modifications and variations are intended to be included herein within the scope of this disclosure.

We claim:
1. A composition comprising:
    a nanoparticle including a siRNA-cationic lipid conjugate, wherein the nanoparticle has a lipid monolayer enclosing a nanoparticle core, wherein the siRNA-cationic lipid conjugate is disposed within the nanoparticle core, wherein the lipid monolayer is selected from the group consisting of: lecithin, phosphatidylcholines, phosphatidic acid, phosphatidylethanolamines, phosphatidylglycerols, phosphatidylserines, phosphatidylinositols, cardiolipins, lipid-polyethyleneglycol conjugates, and a combination thereof,
wherein the nanoparticle core includes a liquid lipid, and
wherein the liquid lipid is a lipid extracted from adipose tissue.

2. The composition of claim 1, wherein the liquid lipid is a lipid extracted from human adipose tissue.

3. The composition of claim 1, wherein the nanoparticle has a diameter of about 150 to 800 nm.

4. The composition of claim 1, wherein the nanoparticle core includes an agent selected from the group consisting of: a drug, an imaging agent, a nonionic surfactant, other types of lipids, and a combination thereof.

5. The composition of claim 1, wherein the outside surface of the lipid monolayer includes an agent selected from the group consisting of: a drug, an imaging agent, a biocompatibility agent, a targeting agent, and a combination thereof.

6. A composition, comprising a nanoparticle including a siRNA-cationic lipid conjugate, wherein the nanoparticle has a lipid monolayer enclosing a nanoparticle core, wherein the siRNA-cationic lipid conjugate is disposed within the nanoparticle core,
wherein the nanoparticle core includes a liquid lipid, and
wherein the liquid lipid is a lipid extracted from adipose tissue,
wherein the cationic lipid is selected from the group consisting of: DOTAP, DC-Cholesterol, DODAP, DDAB, Ethyl PC, DOTMA, and a combination thereof.

* * * * *